United States Patent

Hampton et al.

[11] 4,053,235
[45] Oct. 11, 1977

[54] DIGITAL REFLECTION DENSITOMETER SYSTEM

[75] Inventors: Perry Dwaine Hampton, Dallas; James R. Cox, Richardson, both of Tex.

[73] Assignee: Cosar Corporation, Garland, Tex.

[21] Appl. No.: 355,024

[22] Filed: Apr. 27, 1973

[51] Int. Cl.² .......................... G01J 3/50; G01N 21/48
[52] U.S. Cl. ...................................... 356/188; 356/210
[58] Field of Search .................... 350/315, 317, 318; 356/184, 185, 186, 188, 201–206, 209–212

[56] References Cited

U.S. PATENT DOCUMENTS

| | | | |
|---|---|---|---|
| 2,311,101 | 2/1943 | Tuttle et al. | 356/210 |
| 3,367,230 | 2/1968 | Williams | 356/209 X |
| 3,473,878 | 10/1969 | Schweitzer | 356/210 |
| 3,504,981 | 4/1970 | Malvin | 356/188 X |
| 3,572,944 | 3/1971 | Hanline et al. | 356/206 |
| 3,715,163 | 2/1973 | Mitchell | 356/85 |
| 3,734,630 | 5/1973 | McIntosh et al. | 356/212 X |
| 3,771,877 | 11/1973 | Rosencranz | 356/209 X |

*Primary Examiner* — F. L. Evans
*Attorney, Agent, or Firm* — Richards, Harris & Medlock

[57] ABSTRACT

A digital reflection densitometer system comprises a power supply unit and a digital reflection densitometer instrument which is connected to the power supply unit by means of an electrical cable. The instrument is manually positionable over a surface and includes a housing which is supported on a foot. The foot is adapted for engagement with the surface and includes target apparatus for designating a predetermined area of the surface. The housing is normally pivotally separated from the foot by a spring and is manually pivotable to an operating position adjacent the foot.

A plurality of lamps are mounted in the housing for illuminating the predetermined area of the surface when the housing is in the operating position. Light reflected from the predetermined area is directed through an optical system to a light sensitive apparatus comprising a planar silicon sensor. The output of the planar silicon sensor is directed through an operational amplifier and a logarithmic amplifier to a digital volt meter which actuates a digital display device mounted in the housing of the instrument to provide a visual digital readout indicative of the output of the planar silicon sensor. The instrument further includes apparatus for selectively positioning any one of a plurality of filters in the path of light passing through the optical system to the planar silicon sensor, and for simultaneously adjusting the gain of the operational amplifier and the sensitivity of the digital volt meter to compensate for differences between the filters.

1 Claim, 11 Drawing Figures

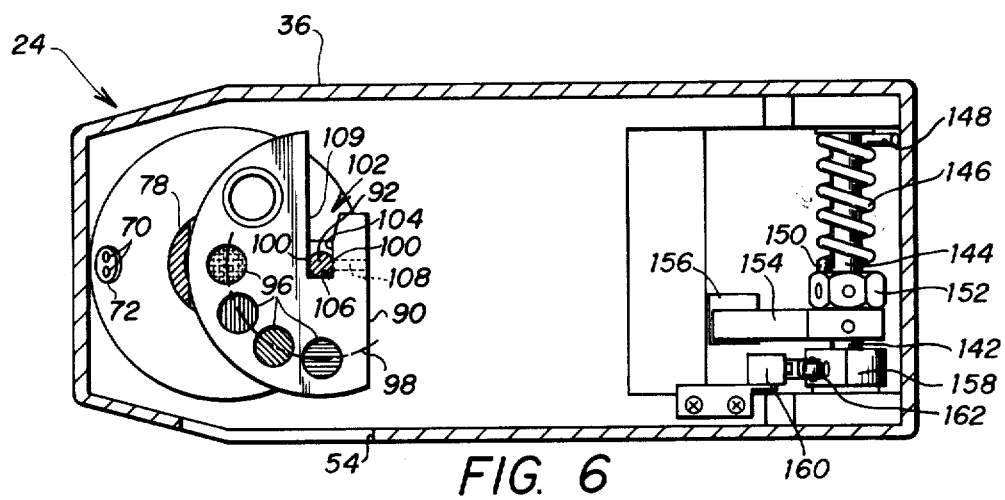
FIG. 6
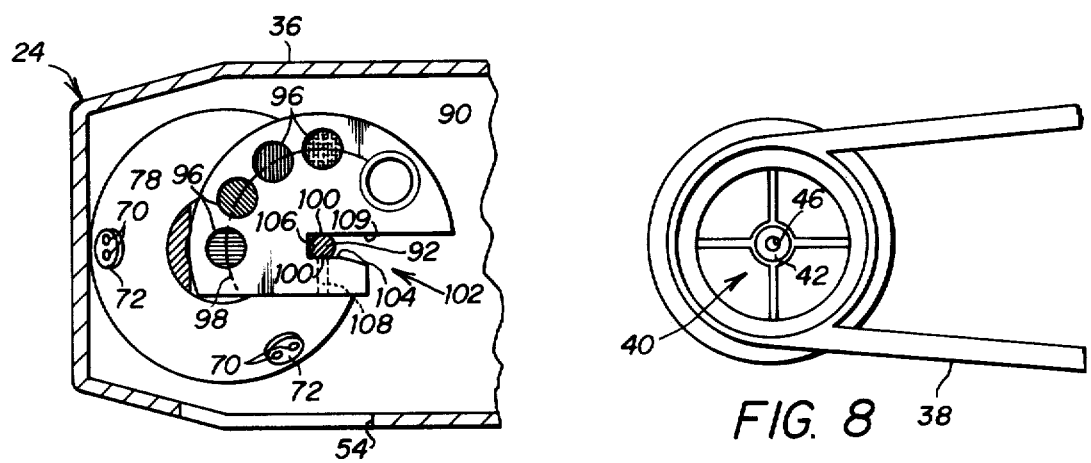
FIG. 7
FIG. 8
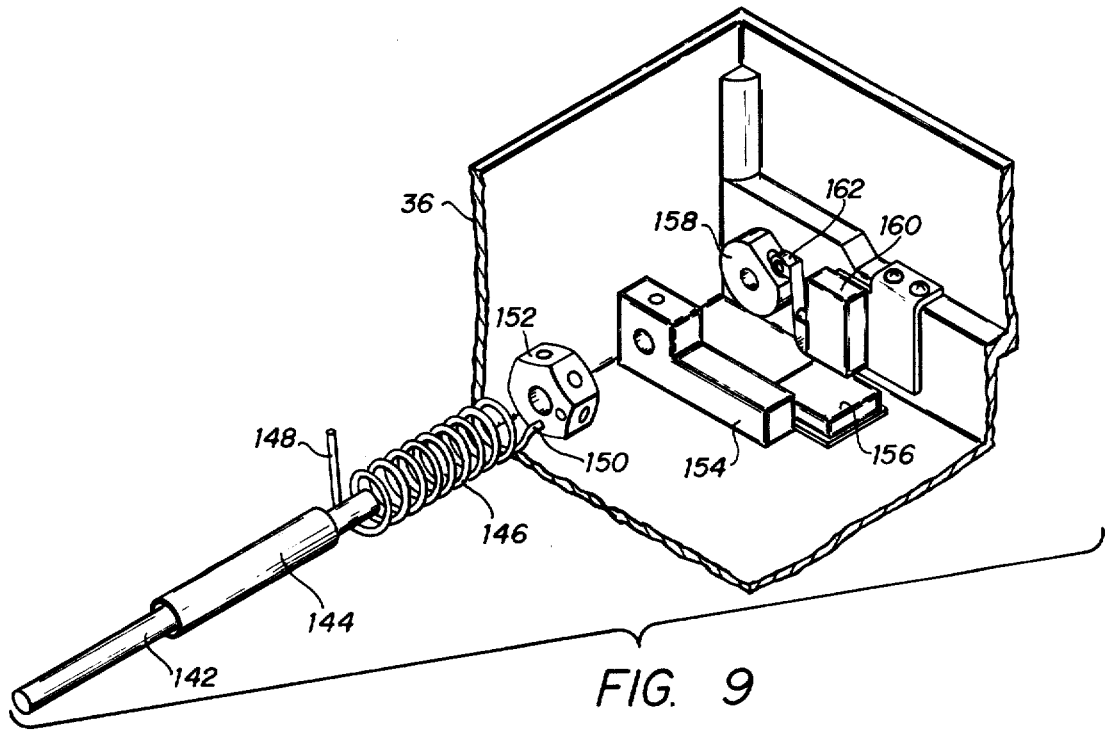
FIG. 9

DIGITAL REFLECTION DENSITOMETER SYSTEM

BACKGROUND AND SUMMARY OF THE INVENTION

This invention relates to a digital reflection densitometer system, and more particularly to a reflection densitometer which is both highly accurate and reliable in operation and extremely convenient to use.

Reflection densitometers are used in the graphic arts industry to perform a variety of functions. For example, color printing sheets are typically provided with a strip extending along one edge including bars of pure color, for example, black and shades of blue, red and yellow. When a particular sheet of this type has been approved for production, the color density of these color bars is determined with a reflection densitometer. Thereafter, during production runs, the color bars along the edges of corresponding printed sheets are checked with a reflection densitometer to assure that the approved color densities are being maintained.

Another use for reflection densitometers is in the area of photography. A reflection densitometer may be used to determine the density of the brightest or "highlight" areas and the darkest or "shadow" areas of the subject to be photographed. These values are then utilized in adjusting the exposure controls of the camera and thereby assuring a correct exposure.

Still another use of reflection densitometers relates to color film processing. Color film manufacturers provide test strips which if processed properly will bear color bars having known densitometer readings. These test strips may therefore be utilized to check the operating parameters of a processing system before the system is used to process exposed film.

It has been found that in order to facilitate the foregoing and similar operations, there are several characteristics which are highly desirable in a reflection densitometer. First, the instrument must be capable of providing highly accurate readings, and must be adapted for long term, essentially maintence free service. Second, the instrument should be adapted for one hand operation, since it is frequently necessary to take readings with one hand while simultaneously recording the reading with the other hand. Third, filter replacements, calibrations, and similar operations should be facilitated with a minimum of down time and inconvenience.

The present invention comprises a reflection densitometer which fulfills all of the foregoing requirements. In accordance with the broader aspects of the invention, all of the operating apparatus, substantially all of the controls, and the readout of a reflection densitometer are mounted in a single housing which is adapted for one hand manipulation over a surface. The operating apparatus includes a plurality of lamps for illuminating a predetermined area of the surface and a planar silicon sensor for producing an output indicative of the intensity of light reflected from the predetermined area of the surface. Switching apparatus is mounted on the housing and is adapted to position any one of a plurality of filters in the path of light passing to the planar silicon sensor, and to similtaneously regulate the operation of electronic circuitry coupled to the output of the planar silicon sensor. The electronic circuitry functions to drive a digital display mounted in the housing and adapted to provide a digital visual readout indicative of the output of the planar silicon sensor.

In accordance with more specific aspects of the invention, an optical system is mounted in the housing for directing light reflected from the predetermined area of the surface along an optical axis to the planar silicon sensor. The switching apparatus includes a shaft extending parallel to the optical axis, and a filter wheel secured to the shaft for rotation therewith to position any one of the filters within the optical system and in alignment with the optical axis thereof. The filter wheel includes a slot which receives the shaft to locate the filters relative to the axis of rotation of the shaft. The housing is provided with a slot which permits insertion, installation, and removal of the filter wheel and which provides access to a set screw adapted to secure the filter wheel to the shaft.

The electronic circuitry of the reflection densitometer comprises an operational amplifier coupled to the output of the planar silicon sensor, a logarithmic amplifier coupled to the output of the operational amplifier, and a digital volt meter coupled to the output of the logarithmic amplifier. The switching apparatus includes switches responsive to the rotational positioning of the shaft for varying the gain of the operational amplifier and for adjusting the sensitivity of the digital volt meter in accordance with the particular filter which is positioned within the optical system. The digital display device comprises a plurality of light emitting diodes which are driven by the digital volt meter to provide the digital visual readout.

In accordance with still other aspects of the invention, a foot is pivotally supported on the housing for engagement with the surface. The foot includes a target portion for designating the predetermined area of the surface. A spring is provided for normally pivotally separating the housing and the foot, however, the housing is adapted for manual pivotal movement into an operating position adjacent the foot against the action of the spring. The lamps are normally operated in a relatively low intensity state and are actuated to a relatively high intensity operating state whenever the housing is pivoted into the operating position.

Operating power for the lamps, the planar silicon sensor, the electronic circuitry, and the digital display device is provided by an electronic power supply. The power supply is mounted within a second housing which is connected to the first housing by means of an electrical cable of substantial length. This arrangement has been found to be highly satisfactory in that it substantially reduces both the weight and the bulk of the portion of the apparatus which is manipulated in order to make reflection densitometer readings, and yet does not sacrifice the convenience which is obtained by mounting all of the operating apparatus, substantially all of the controls, and the readout of the reflection densitometer within the same housing.

DESCRIPTION OF THE DRAWINGS

A more complete understanding of the invention may be had by referring to the following Detailed Description, when taken in conjunction with the accompanying Drawings, wherein:

FIG. 6 is a sectional view taken generally along the line 6—6 in FIG. 4 and illustrating the positioning of the component parts for installation and removal of the filter wheel;

FIG. 7 is a view similar to FIG. 6 illustrating the positioning of the component parts of the instrument for securing the filter wheel to the shaft;

FIG. 8 is a top view of the foot of the instrument;

FIG. 9 is an exploded perspective view illustrating the spring biasing apparatus, the stop apparatus, and the lamp intensity control switch apparatus of the instrument;

DETAILED DESCRIPTION

Figure 1:
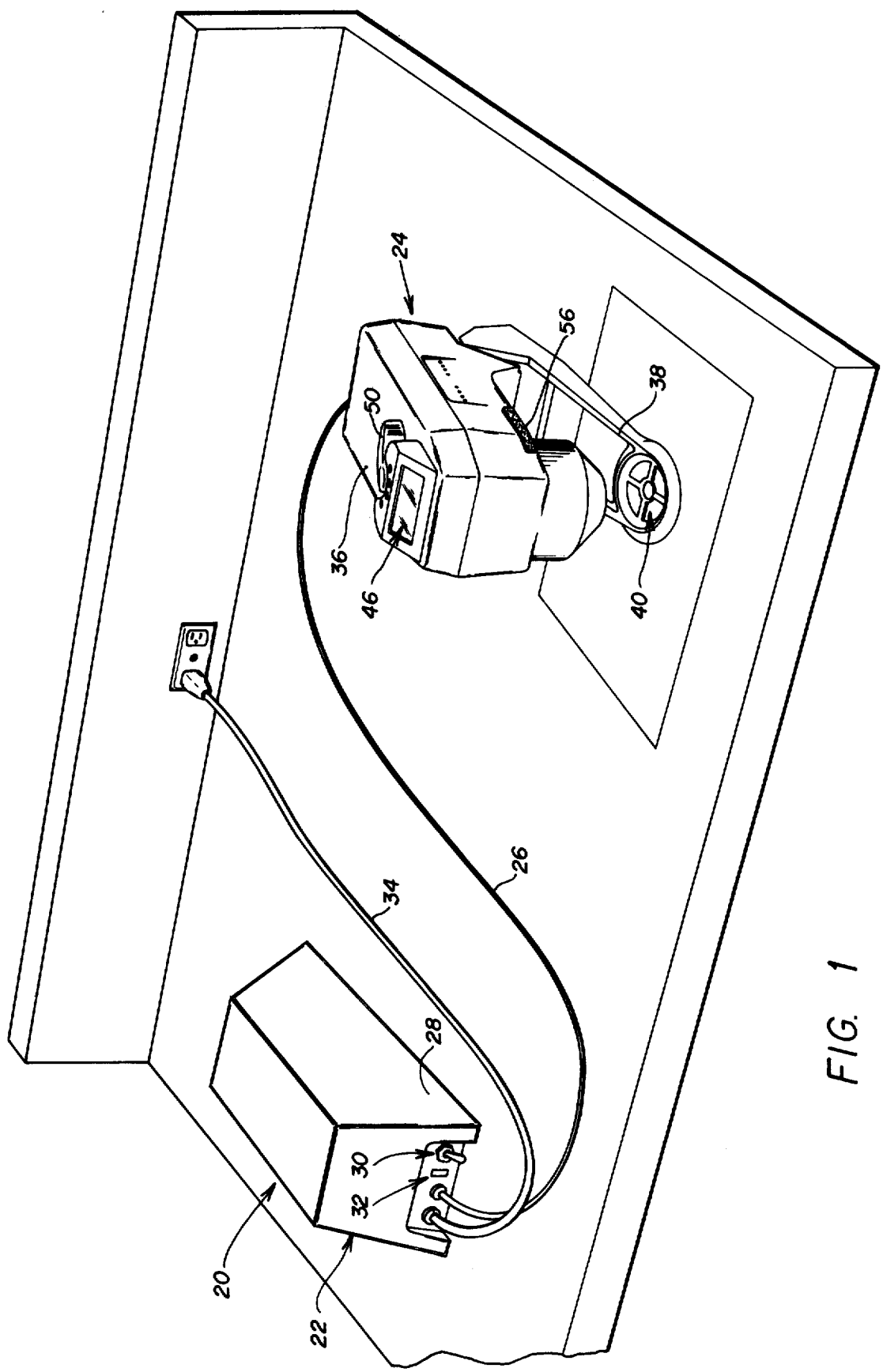
FIG. 1 is a perspective view of a digital reflection densitometer system incorporating the invention.

Referring now to the Drawings, and particularly to FIG. 1 thereof, there is shown a digital reflection densitometer system 20 incorporating the invention. The system 20 comprises a power supply unit 22 and a digital reflection densitometer instrument 24 which is connected to the power supply unit 22 by means of an electrical cable 26. The instrument 24 is adapted for manual positioning relative to a surface S to be measured, and comprises all of the operating apparatus, substantially all of the controls, and the readout of the digital reflection densitometer system 20. The power supply unit 22 comprises a conventional electronic power supply circuit contained within a housing 28. The unit 22 further comprises a conventional off-on switch 30 and a switch 32 for selectively placing the system either in a 115 volt operating mode or in a 230 volt operating mode. Operating power for the digital reflection densitometer system 20 is received in the power supply unit 22 by means of a conventional line cord 34.

Figure 2:
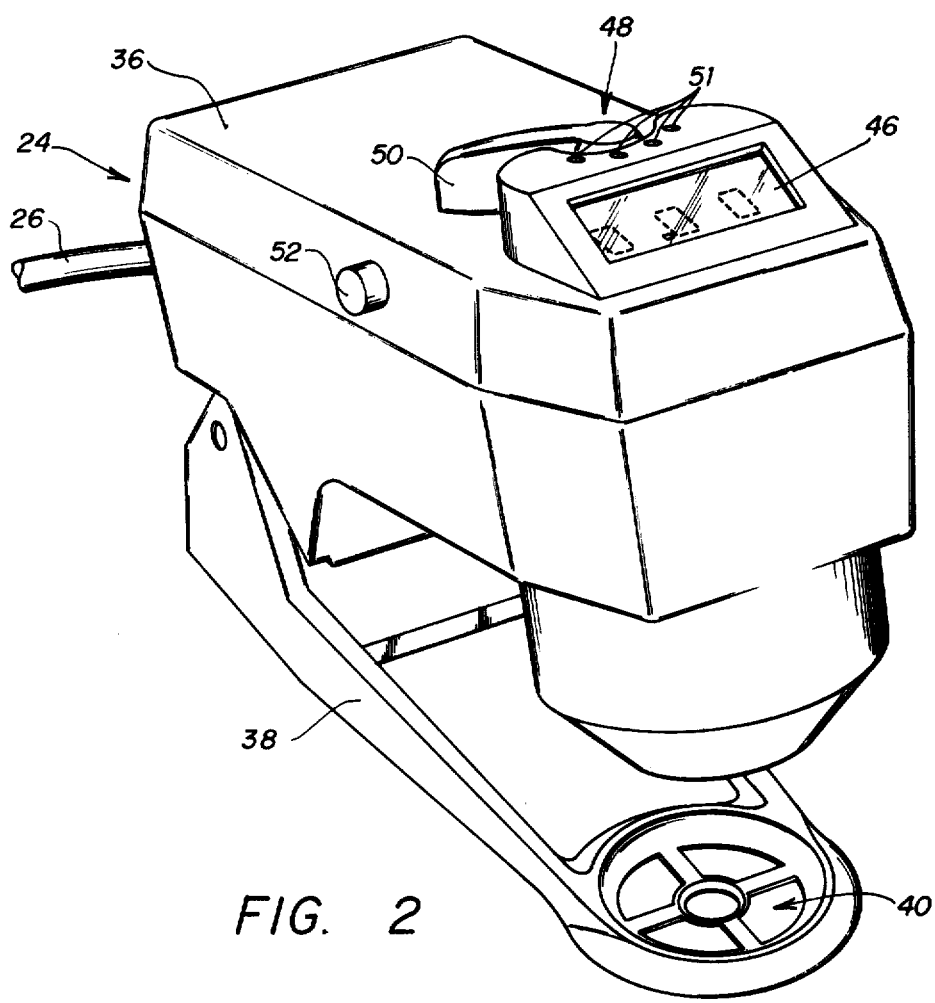
FIG. 2 is a perspective view of the digital reflection densitometer instrument of the system shown in FIG. 1.
Figure 3:
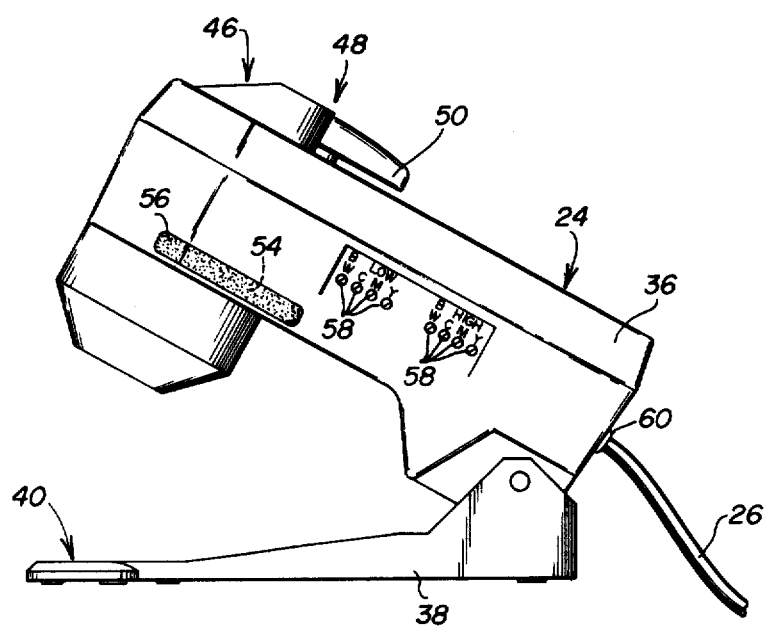
FIG. 3 is a side view of the instrument.

As is best shown in FIGS. 2 and 3, the digital reflection densitometer instrument 24 of the system 20 comprises a housing 36 and a foot 38 that is pivotally connected to the housing 36 and adapted for engagement with the surface S. The foot 38 extends to a target portion 40 which functions to designate a predetermined area of the surface S. As is best shown in FIGS. 4 and 8, the foot 38 may be provided with a replaceable final target member 42 having a small circular aperture 44 formed therein.

Referring again to FIGS. 2 and 3, the digital reflection densitometer instrument 24 further comprises a digital display device 46 positioned at the upper front corner of housing 36. A filter selection apparatus 48 for the instrument 24 includes an operating handle 50 mounted on the top of the housing 36 just behind the display device 46 and a plurality of filter section indicia located at spaced intervals around the handle 50. An enable button 52 projects from one side of the upper portion of the housing 36.

A filter wheel installation/removal slot 54 is provided in the opposite side of the housing 36 and is normally covered by a dust cap 56. A plurality of adjustment screws 58 are accessible from the same side of the housing 36 and are utilized in the calibration of the instrument 24. The electrical cable 26 which connects the instrument 24 to the power supply unit 22 enters the housing 36 through a grommet 60 mounted in the rear wall of the housing.

Figure 4:
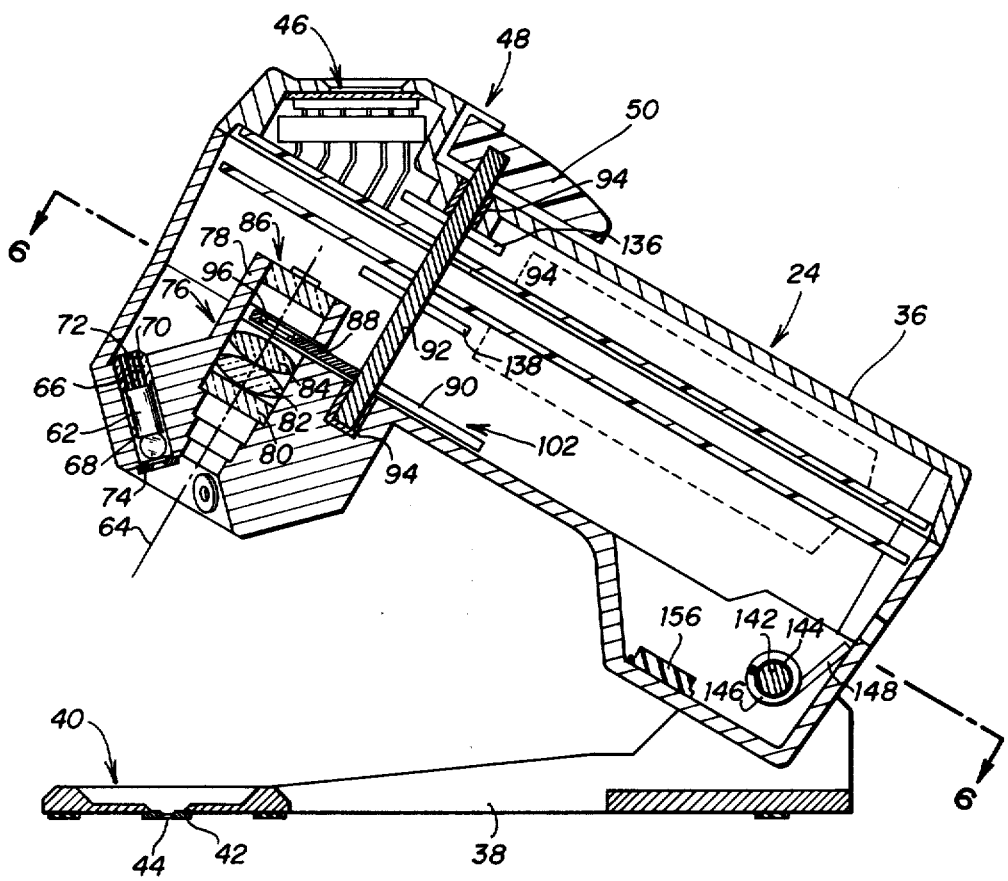
FIG. 4 is a longitudinal sectional view of the instrument showing the instrument in the normal position.
Figure 5:
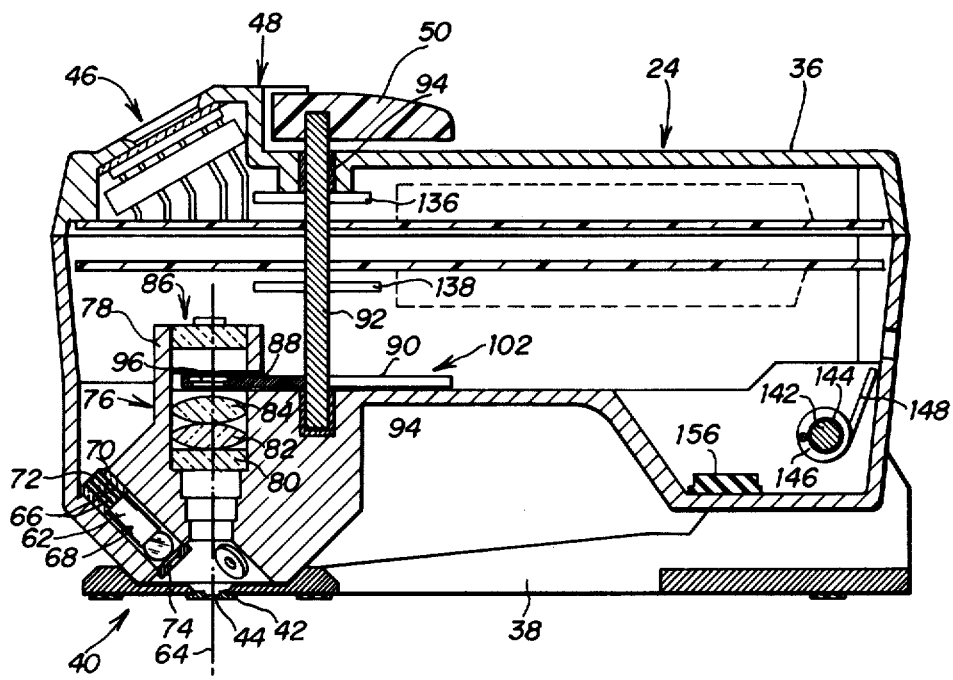
FIG. 5 is a view similar to FIG. 4 showing the instrument in the operating position.

The operating apparatus of the digital reflection densitometer instrument 24 is best shown in FIGS. 4 and 5. A plurality of lamps 62 are mounted at equally spaced intervals about an optical axis 64. Each lamp 62 is fabricated by positioning the lamp in a jig, prefocusing the lamp, and then potting the lamp with epoxy to maintain the focus thereof. A pair of pins 66 extend from the rear of each lamp 62.

The lamps 62 are mounted in lamp receiving cylinders 68 formed in the housing 36 of the instrument 24. The lamps 62 are both installed in and removed from the cylinder 68 by means of a small rubber tube which receives the operating end of the lamp. As the lamp 62 is inserted into the cylinder 68, the pins 66 of the lamp engage aligned conductive sockets 70 comprising part of a lamp socket 72 mounted in the housing 36, whereby operating power is supplied to the lamp. After the lamp 62 is installed, a small cap 74 is mounted in the open end of the cylinder 68 to restrict the beam of the lamp. In those applications of the system in which the target member 42 is not used, the caps 74 are also not used.

The optical axis 64 is defined by an optical system 76 which is mounted in an optics housing 78 comprising an internal portion of the housing 36. The optical system 76 includes a filter 80, a lens 82, and a lens 84, and functions to direct light reflected from the predetermined portion of the surface to a light sensitive apparatus 86 mounted in the upper end of the housing 78.

The optics housing 78 has a slot 88 formed in it, and a filter wheel 90 is supported for rotation in slot 88. The filter wheel 90 is mounted on a shaft 92 which is in turn supported by a pair of bushings 94 for rotation about an axis extending parallel to the optical axis 64. As is best shown in FIG. 6, a plurality of filters 96 are mounted in the filter wheel 90 at spaced points about an arc 98 extending concentrically with the axis of rotation of the shaft 92. Therefore, upon manipulation of the handle 50 of the filter selection apparatus 48, the shaft 92 and the filter wheel 90 function to selectively position any one of the filters 96 within the optical system 76 and in alignment with the optical axis 64 thereof. It will be understood that alignment of the handle 50 with a particular indicia 51 on the upper surface of the housing 36 is effective to position a selected filter 96 in the path of light passing through the optical system to the light sensitive apparatus 86.

The shaft 92 includes at least a portion having opposed, flat sides 100. The filter wheel 90 includes a slot 102 defined by opposed edges 104 and a locating surface 106. The edges 104 of the slot 102 engage the flat sides 100, and the locating surface 106 engages the shaft 92 to precisely locate the filter wheel 90 such that the arc 98 is exactly concentric with the axis of rotation of the shaft 92. The filter wheel installation/removal slot 54 of the housing 36 is located such that when the shaft 92 and the filter wheel 90 are positioned as shown in FIG. 6, the filter wheel 90 may be installed in or removed from the digital reflection densitometer instrument 24.

A set screw 108 is threadedly received in the filter wheel 90 for use in securing the filter wheel 90 to the shaft 92. The positioning of the set screw 108 is such that when the shaft 92 is rotated through approximately 90° from the position shown in FIG. 6 to the position shown in FIG. 7, the set screw 108 is aligned with the slot 54. A suitable tool is then inserted through the slot 54 for the purpose of either tightening or loosening the set screw 108.

Figure 11:
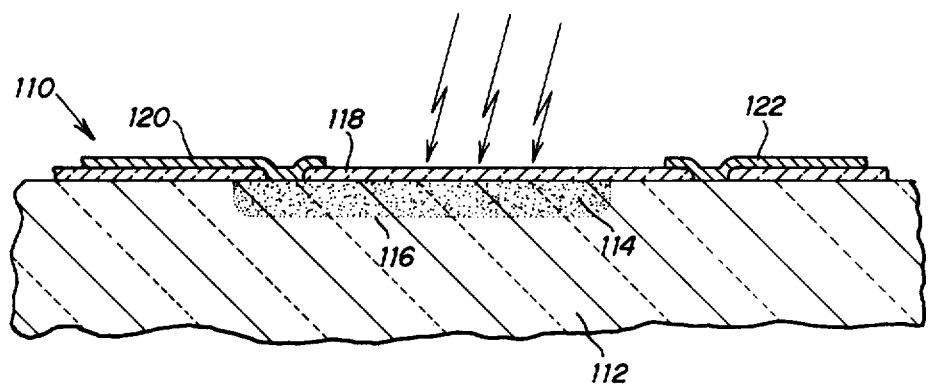
FIG. 11 is a schematic illustration of the light sensitive apparatus of the digital reflection densitometer system.

The light sensitive apparatus 86 of the digital reflection densitometer instrument 24 preferably comprises a planar silicon sensor, such as the planar silicon sensor 110 illustrated in FIG. 11. The planar silicon sensor 110 includes a body of semiconductor material 112 comprising a first type, for example, p-type semiconducter material. The body 112 has a region 114 formed therein comprising a different type semiconducter material, for example, n-type semiconductor material. The interface of the body 111 and the region 114 thus define a semiconductor junction 116.

A layer of oxide material 118 is formed across the surface of a body of semiconductor material 112 and is etched to provide access to the main portion of the body of the semiconductor material 112 and the region 114 thereof. Metal leads 120 and 122 are then deposited on top of the oxide layer and into the etched regions to provide electrical contact with the opposite sides of the junction 116. The planar silicon sensor 110 is thus adapted to establish an electrical signal across the leads 120 and 122 in response to received light as indicated by the arrows in FIG. 11.

Those skilled in the art will appreciate the fact that the planar silicon sensor 110 may be operated either in the photovoltaic mode in which case an output current is generated in response to received light, or as a photodiode. In accordance with the present invention, the planar silicon sensor 110 is preferably operated in the photovoltaic mode. This is because when it is operated in this mode, the planar silicon sensor 110 produces an output current which is directly proportional to the intensity of the received light. Moreover, when operated in the photovoltaic mode, the planar silicon sensor 110 is highly nonresponsive to temperature changes insofar as its operating characteristics are concerned.

Figure 10:
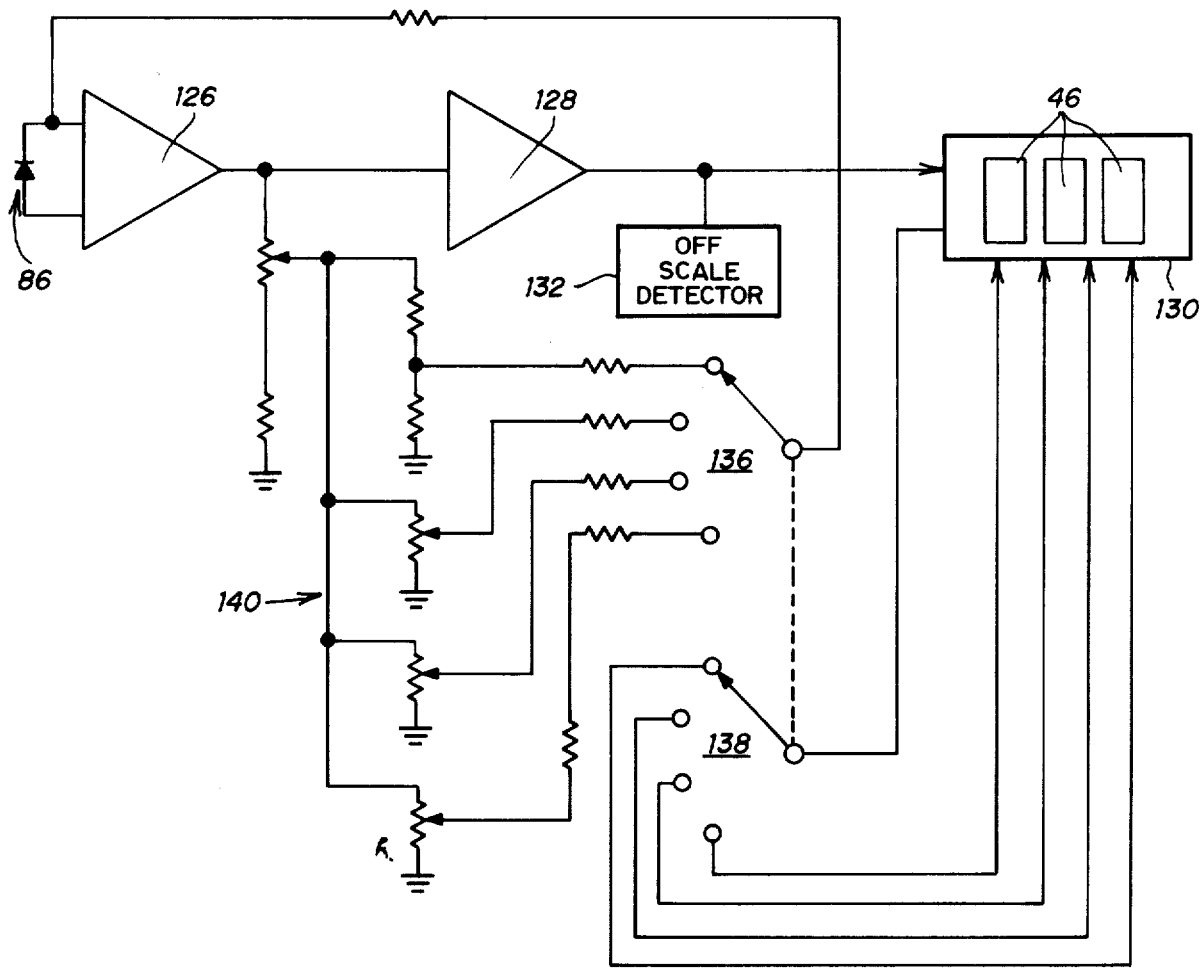
FIG. 10 is a schematic illustration of the electronic circuitry contained within the instrument of the digital reflection densitometer system.

Referring now to FIG. 10, the output of the planar silicon sensor comprising the light sensitive apparatus 86 of the digital reflection densitometer instrument 24 is directed to an operational amplifier 126. As is well known, such an apparatus may be operated to provide an output voltage which is proportional to the magnitude of the input current. The output signal from the operational amplifier 126 is directed to a logarithmic amplifier 128, which produces an output comprising the logarithm of the output signal from the amplifier 126 minus a reference signal, and the output of the logarithmic amplifier 128 is in turn directed to a digital volt meter 130. The digital volt meter 130 in turn actuates the digital display device 46 of the instrument 24. The digital display device 46 actually comprises three sets of light emitting diodes each arranged to illuminate any of the ten conventional digits in accordance with the output of the digital volt meter 130. By this means the digital display device 46 functions to provide a visual digital readout indicative of the output of the light sensitive apparatus 86 of the instrument 24, and thus indicative of the optical density of the particular area of the surface S under examination.

The electronic circuitry of the digital reflection densitometer instrument 24 further includes an off scale detector 132 which functions to flash the digital display device 46 whenever the instrument is actuated to measure an optical density which would be negative based on the calibration of the instrument.

Referring briefly to FIG. 4, the filter selection apparatus 48 further includes two switches 136 and 138 which are actuated in response to the rotational positioning of the shaft 92. Referring again to FIG. 10, the switch 136 operates a gain control network 140, and therefore functions to vary the gain of the operational amplifier 126 in accordance with the particular color filter 96 which is positioned within the optical system 76. Similarly, the switch 138 functions to vary the sensitivity of the digital volt meter 130 in accordance with the particular color filter 96 in use at the time. In this manner the electronic circuitry of the digital reflection densitometer instrument 24 is varied to compensate for differences between the color filters and thereby provide a uniform readout from the instrument.

Referring now to FIG. 9, the housing 36 and the foot 38 of the reflection densitometer instrument 24 are pivotally interconnected by means of a shaft 142. A brass sleeve 144 surrounds the shaft 142, and a spring 146 surrounds the sleeve 144. The spring 146 includes an arm 148 which engages the housing 36 and an arm 150 which engages a spring holder 152. The spring holder 152 is mounted on the shaft 142 and is secured to the shaft 142 by means of set screws. The spring 146 therefore functions to bias the housing 36 away from the foot 38 and to normally position the housing 36 and the foot 38 in the pivotally separated position illustrated in FIGS. 3 and 4. It will be understood, however, that the housing 36 is manually pivotable on the shaft 142 against the action of the spring 146 from the normal position illustrated in FIG. 4 to the operating position illustrated in FIG. 5.

A stop arm 154 is also mounted on the shaft 142 and secured thereto by means of set screws. The stop arm 154 is positioned for engagement with a rubber stop pad 156 mounted in the housing 36 and therefore serves to limit pivotal movement of the housing 36 relative to the foot 38 under the action of the spring 146.

The shaft 142 further supports a cam 158. Like the spring holder 152 and the stop arm 154, the cam 158 is secured to the shaft 142 by means of set screws. A limit switch 160 including a cam follower roller 162 is mounted in the housing 36 for pivotal movement therewith against and with the action of the spring 146. The limit switch 160 therefore serves to provide an output indicative of the relative pivotal positioning of the housing 36 with respect to the foot 38.

The lamps 62 of the digital reflection densitometer instrument 24 are operated in a relatively low intensity condition whenever the off-on switch 30 of the power supply unit 22 is in the "on" condition and the housing 36 is in the normal position illustrated in FIG. 4 of the Drawings. As the housing 36 is pivoted from the position shown in FIG. 4 to the operating position shown in FIG. 5, the cam 158 actuates the switch 160, which in turn functions to increase the operating intensity of the lamps 62. By this means the lamps 62 are operated in a relatively low intensity condition at all times except when the digital reflection densitometer system 20 is actuatally in use. The effective operating life of the lamps 62 is thus substantially increased over that which would be experienced if the lamps were operated in the high intensity condition at all times.

OPERATION

The use of the digital reflection densitometer system 20 will be best understood by referring again to FIG. 1. The power supply unit 22 of the system is positioned adjacent a work station, and the digital reflection densitometer instrument 24 of the system is manipulated to position the target portion 40 of the foot 38 in alignment with a particular area of the surface S to be measured.

For example, in the case of color printing, the target 40 will be positioned in alignment with one of the color bars adjacent the edge of the printed sheet. At the same time the handle 50 of the filter selection apparatus 48 is manipulated to position the selected filter 96 in the optical system 76 and in alignment with the optical axis 64 thereof.

At this point the housing 36 of the instrument 24 is pivoted downwardly against the action of the spring 146 until the housing 36 is positioned in the operating position illustrated in FIG. 5. This actuates the switch 160 to operate the lamps 62 at the operating intensity. By this means the selected area of the surface S is fully illuminated during the measuring operation.

At this point the button 52 is actuated to enable the digital display 46 of the instrument 24. Light reflected from the predetermined area of the surface passes upwardly through the optical system 76 and the selected filter 96 and is received by the planar silicon sensor comprising the light sensitive apparatus 86. The output of the planar silicon sensor is amplified by the operational amplifier 126 and by the logarithmic amplifier 128 and is received by the digital volt meter 130, whereupon the digital display device 46 is actuated to provide a visual digital readout indicative of the optical density of the predetermined area of the surface. It should be noted in this regard that the switches 136 and 138 function to vary the gain of the operational amplifier 126 and the sensitivity of the digital volt meter 130 in accordance with differences between the individual color filters 96 of the instrument.

Those skilled in the art will appreciate the fact that it is considered desirable to check the calibration of a reflection densitometer from time to time. In accordance with the reflection densitometer system incorporating the present invention, the calibration check is preferably performed on a daily basis. The calibration operation is performed by means of the screws 58 of the instrument 24, and utilizing the Reflection Densitometer Calibration System disclosed and claimed in the co-pending application of James R. Cox, filed Apr. 27, 1973, Ser. No. 355,023, the disclosure of which is incorporated herein by reference.

From the foregoing, it will be understood that the present invention comprises a digital reflection densitometer incorporating numerous advantages over the prior art. Perhaps the most important advantage deriving from the use of the invention comprises the fact that reflection densitometers constructed in accordance with the invention are adapted to provide extremely accurate readings, and are simultaneously adapted to provide long term, substantially maintenance free service. Another advantage relates to the fact that reflection densitometer systems incorporating the invention include a reflection densitometer instrument adapted for one hand operation and comprising all of the operating apparatus, substantially all of the controls, and the entire readout apparatus of the system. This feature of the invention renders the use of reflection densitometers incorporating the invention highly convenient. Still another advantage deriving from the use of the invention relates to the fact that the filter replacement and/or calibration operations which are periodically required in the operation of a reflection densitometer are carried out in instruments incorporating the present invention with a minimum of inconvenience and a minimum of down time.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

What is claimed is:

1. In a reflection densitometer, the improvement comprising:
    a housing adapted for manual positioning over a surface;
    an optical system mounted in the housing and having a predetermined axis for receiving the light reflected from the predetermined portion of the system;
    a plurality of lamp receiving cylinders formed in said housing at spaced points around the axis of the optical system;
    a plurality of lamps for detachably fitting within said cylinders for illuminating the predetermined area of the surface;
    each of said lamps having a pair of pins extending from the rear thereof;
    a lamp socket mounted in each of said cylinders and having conductive sockets connected to a source of power for receiving said pins of said lamps;
    light sensitive means mounted within the housing on the axis of the optical system for receiving reflected light passing through the optical system and for generating an output in accordance with the intensity of the received light;
    optical filter means for selective positioning within the optical system and in alignment with the axis thereof;
    electronic circuitry means mounted within said housing for receiving the output of said light sensitive means for generating a digital output indicative of the output of the light sensitive means;
    said electronic circuitry including an operational amplifier coupled across the output of said light sensitive means for producing an output voltage proportional to the output current produced by the light sensitive means;
    a logarithmic amplifier connected to the output of the operational amplifier;
    digital volt meter means connected to the output of the logarithmic amplifier; and
    digital display means including light emitting diodes mounted in the housing for actuation by the output of the digital volt meter means to provide a digital visual readout on said housing indicative of the output of the light sensitive means.

* * * * *